(12) United States Patent
Soto et al.

(10) Patent No.: US 8,944,681 B2
(45) Date of Patent: Feb. 3, 2015

(54) MOBILE X-RAY MACHINE WITH AN ANTICOLLISION DEVICE

(75) Inventors: Jose Emilio Soto, Buc (FR); Francis Guerit, Buc (FR); Guy Bertrand, Buc (FR); Bruno Galloni, Buc (FR); Bernard Bouvier, Buc (FR)

(73) Assignee: General Electric Company, Schenectady, NY (US)

( * ) Notice: Subject to any disclaimer, the term of this patent is extended or adjusted under 35 U.S.C. 154(b) by 317 days.

(21) Appl. No.: 13/463,057

(22) Filed: May 3, 2012

(65) Prior Publication Data

US 2013/0294584 A1 Nov. 7, 2013

(51) Int. Cl.
*H05G 1/02* (2006.01)

(52) U.S. Cl.
USPC ............................ 378/198; 378/102

(58) Field of Classification Search
CPC .................................... A61B 6/4405
USPC ................................ 378/102, 198
See application file for complete search history.

(56) References Cited

U.S. PATENT DOCUMENTS

| 7,046,764 | B1 | 5/2006 | Kump | |
|---|---|---|---|---|
| 7,377,172 | B2 * | 5/2008 | Jensen et al. | 73/702 |
| 2008/0013692 | A1 | 1/2008 | Maschke | |
| 2008/0123811 | A1 | 5/2008 | Curtis | |
| 2008/0304626 | A1 | 12/2008 | Camus | |

FOREIGN PATENT DOCUMENTS

| EP | 1479343 A1 | 11/2004 |
|---|---|---|
| EP | 1152438 | 3/2011 |

OTHER PUBLICATIONS

Search Report and Written Opinion from corresponding French application No. 1152438, dated Sep. 5, 2011.

* cited by examiner

*Primary Examiner* — Hoon Song
(74) *Attorney, Agent, or Firm* — GE Global Patent Operation; Marc A. Vivenzio

(57) ABSTRACT

An X-ray machine is provided. The X-ray machine comprises an X-ray tube; an X-ray detector placed opposite the X-ray tube in a direction of emission of X-rays; and a mobile device on which the X-ray tube and the X-ray detector are mounted, the mobile device comprising a motor capable of causing the automatic movement of the X-ray machine, and an impact-sensing system coupled to the motor in order to control the movement of the mobile device in the event of an impact applied to the X-ray apparatus.

8 Claims, 3 Drawing Sheets

MOBILE X-RAY MACHINE WITH AN ANTICOLLISION DEVICE

BACKGROUND OF THE INVENTION

1. Field of the Invention

The field of invention relates generally to X-ray machines and to X-ray machines used in the field of medical imaging. The field of invention relates more particularly to X-ray machines that are mounted on a mobile device.

2. Description of Related Art

X-ray machines conventionally comprise an X-ray tube and an X-ray detector placed opposite the X-ray tube in the direction of emission of the X-rays. The tube and the detector are usually placed on opposite ends of an arm.

Such machines are used for angiographic examinations with a diagnostic or interventional aim. During these examinations, it is necessary to take X-ray radiographs of an area of interest in the body of a patient. For this purpose, after the patient has been laid out on an examination table, the X-ray tube and the detector are brought to face the area to be radiographed.

There are several types of X-ray machines for producing radiographs. First, X-ray machines that are fixed to the ground and in which the arm supporting the X-ray tube and the detector comprise several degrees of freedom making it possible to position the X-ray beam facing the area of interest are known. This type of machine has a major drawback when radiography is necessary only at the beginning and the end of the intervention. In between, access to the patient should take precedence. However, the machine cannot be removed from the examination table when it is not being used. In particular, transferring the patient onto the examination table is hampered by the presence of this bulky system.

There are also X-ray machines called "surgical mobile" units that can be moved manually. In this case, they are mounted on a carriage that contains a certain number of batteries used to supply the X-ray tube with power. This type of machine is not suitable for angiographic examinations because the power available to the X-ray tube is no longer sufficient to obtain adequate image quality and, in particular, contrast. Moreover, this type of mobile X-ray machine does not allow complex angulations because the diameter of the arm supporting the tube and the detector is not large enough. Similarly, these mobile X-ray machines do not achieve sufficient rotation speeds to allow high quality, three-dimensional image reconstructions. Finally, even though the weight of such an X-ray machine is half as much as that of an X-ray machine designed for angiography, it remains very difficult to move because of its relatively large dimensions and weight, which can be up to about 300 kg (about 660 lbs).

In addition, X-ray machines for angiography are known that are suspended from the ceiling and can be moved on guide rails, via a mobile carriage, for example with the aid of an electric motor. This type of machine also has several drawbacks. First, many systems are already attached to the ceiling around the examination table, thus the space around the patient is already cluttered which makes it difficult to install guide rails. Secondly, mounting an X-ray machine on the ceiling considerably increases the risk of opportunistic contamination of the patient. Specifically, because of the difficulty of cleaning the rails, particles are likely to fall and contaminate the patient when the machine is sliding on the rails. Moreover, in certain operating rooms, a sterile laminar flow is generated above the patient. In this case, the flow is likely to blow particles present on the rail which can then enter the laminar flow and reach the patient.

To alleviate these various drawbacks, it has been proposed to mount the X-ray machine on a mobile device mounted on wheels driven by drive motors controlled automatically under the control of a navigation system. It has been found that such a system is particularly effective for moving the X-ray machine in an operating or examination room, notably to position the X-ray tube and the detector around the area of interest and to move it away when it is no longer in use, in order to free up the space around the examination table.

However, this X-ray machine, which is capable of being moved automatically, either in a stand-alone mode, or under the control of a control console that can be operated by an operator, in particular during its return to the out-of-the-way waiting position, is likely to come into contact with elements present on the floor of the operating room, such as control pedals, or to bump into the feet of persons present in the operating room, which, because of the weight of the machine, which may be up to several hundreds of kilos, is likely either to damage the equipment of the operating room, or to cause injuries to the members of medical staff.

In the light of the foregoing, the object of the embodiments of the present invention is to propose an X-ray machine which remedies this drawback and which removes all risk of an accident likely to be caused by its automatic movement in the operating room.

BRIEF SUMMARY OF THE INVENTION

According to one embodiment, an X-ray machine is provided. The X-ray machine comprises an X-ray tube; an X-ray detector placed opposite the X-ray tube in a direction of emission of X-rays; and a mobile device on which the X-ray tube and the X-ray detector are mounted, the mobile device comprising a motor capable of causing the automatic movement of the X-ray machine, and an impact-sensing system coupled to the motor in order to control the movement of the mobile device in the event of an impact applied to the X-ray apparatus.

Further aspects, advantages and features of the present invention are apparent from the dependent claims, the description and the accompanying drawings.

BRIEF DESCRIPTION OF THE SEVERAL VIEWS OF THE DRAWINGS

Other objects, features and advantages of the invention will appear on reading the following description, given only as a non-limiting example and made with reference to the appended drawings in which.

DETAILED DESCRIPTION OF THE INVENTION

Figure 1:
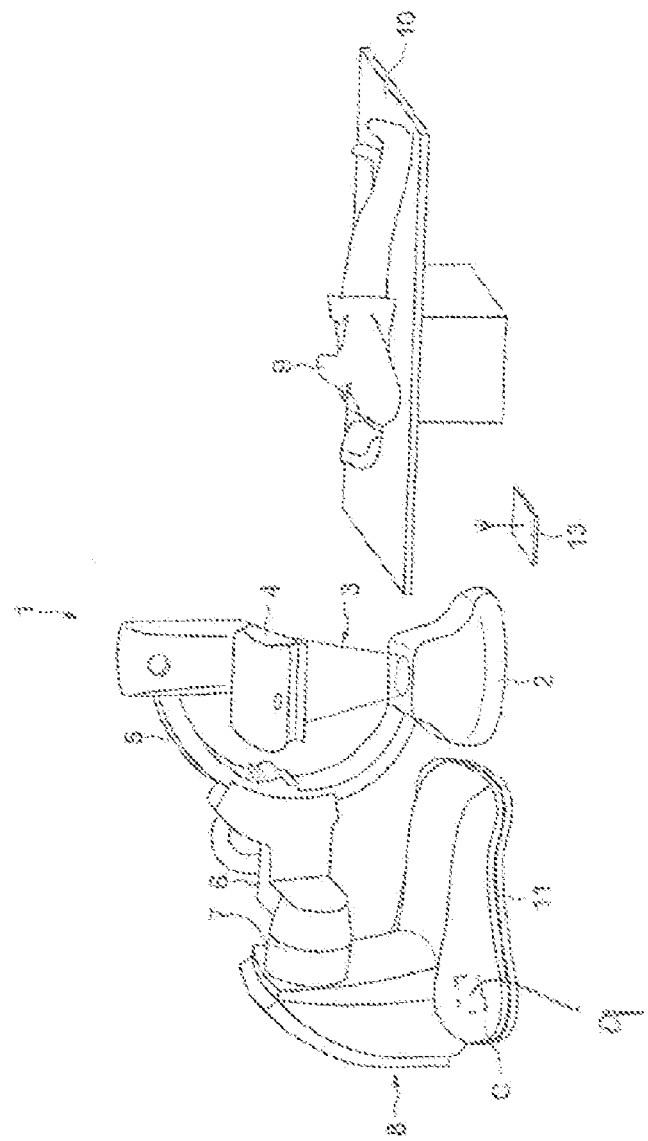
FIG. 1 is a schematic view of an X-ray machine provided with a mobile device fitted with an impact-sensing system according to an embodiment of the invention.

FIG. 1 illustrates an X-ray machine 1 of the vascular type. As can be seen, this machine 1 essentially comprises an X-ray tube 2, capable of emitting a beam 3 of X-rays in an emission direction, and a detector 4 of X-rays, each placed at the opposite ends of an arm 5, in this instance in the shape of an arch, so that the X-rays emitted by the tube 2 are incident on the detector 4. The arm 5 is mounted slidingly on a second arm 6 mounted so as to rotate on a fixed support 7, itself mounted on a mobile device 8. Therefore, the support 7, the rotary arm 6 and the arm 5 are all three articulated relative to one another so that the X-ray machine can be moved in three dimensions and thus produce images of an organ to be examined at various angles of incidence.

During a radiograph, the tube 2 and the detector 4 are brought to face an area of interest of the body 9 of a patient laid out on an examination table 10 so that, when the area of interest is interposed between the X-ray tube 2 and the detector 4, it is irradiated by the X-rays, and the detector 4 produces representative data of features of the interposed area of interest.

The mobile device 8 comprises, in the exemplary embodiment shown, a housing C supported by a running system comprising, for example, two lateral drive and directional wheels placed at the rear, two free front wheels (not visible in FIG. 1), and means for driving the drive wheels placed in the housing C and comprising a directional motor 9 coupled to a drive motor. The mobile device 8 is a programmable device and is associated with a navigation system capable, for example, of communicating by radioelectric link with identification devices 13 placed in the operating room in order to allow the machine 1 to be located precisely in the room and, notably, relative to the examination table 10.

Therefore, according to the programming phases or under the control of a control console that can be operated by an operator, the X-ray machine is capable of being moved automatically in the operating room. This is particularly the case during the positioning of the X-ray machine facing the examination table in order to place the tube 2 and the detector 4 facing an area of interest to be radiographed or during the movement of the X-ray machine to an out-of-the-way waiting position when it is no longer in use.

For the purpose of avoiding any accident in the case of a collision either with equipment, such as control pedals present on the floor of the operating room, or to avoid any injury to a person present in the room, the X-ray machine is provided with an impact-sensing system coupled to the means for driving the drive wheels of the mobile device. This impact-sensing system is provided on the housing C of the mobile device so as to detect the impacts likely to occur during the movement of the machine 1 and cause it to stop, or even to reverse, if an impact is detected. As can be seen in FIG. 1, the impact-sensing system comprises a peripheral sensor 11 mounted in the bottom portion of the housing C, protruding laterally from the latter.

In one embodiment, this peripheral sensor is made in the form of a resistive sensor comprising, for example, a pair of conductive tracks placed in parallel in a rubber sleeve and capable of coming into contact in the event of impact. For example, an impact can then be detected by powering one of the tracks, and by detecting the presence of a current in the other track in the event of the two conductive tracks being placed in localized contact. Naturally, other embodiments of the impact sensor are also possible. Therefore, there is no departure from the context of the invention when other types of sensors, for example optical, inductive, etc. sensors are used that are capable of delivering an impact-detection signal.

The detection signal thus generated can then be transmitted to a control circuit for controlling the means for driving the wheels of the mobile device so as to stop the X-ray machine or drive it in reverse. It will be noted that the embodiment of the impact sensor in the form of a sensor that is for example resistive, provided over the whole periphery of the housing, makes it possible to detect impacts on 360°, irrespective of the point of impact. However, there is no further departure from the context of the invention when the peripheral impact sensor is made in the form of a set of individual sensors distributed over the whole periphery of the housing.

Figure 2:
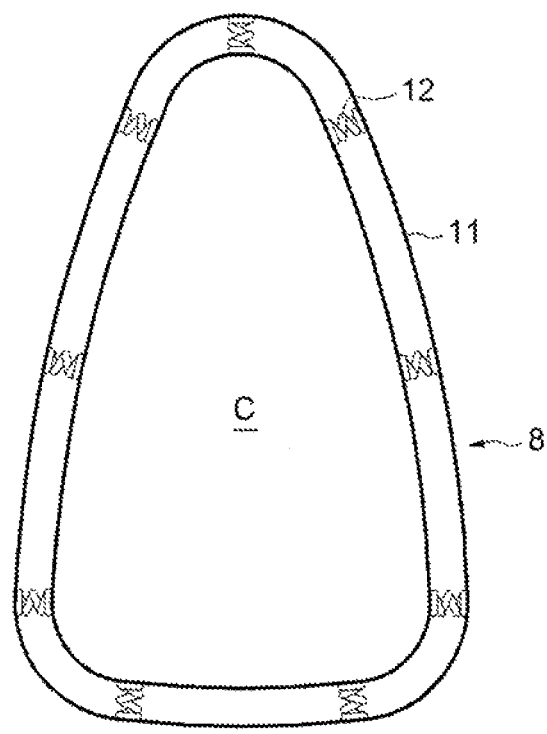
FIG. 2 is a schematic view illustrating the mounting of the impact sensor onto the housing of the mobile device according to an embodiment of the invention.

With reference to FIG. 2, in one embodiment, the peripheral sensor 11 is mounted on the housing C by means of elastically deformable mounting elements, such as 12, in this instance springs evenly distributed between the peripheral sensor 11 and the housing C along its periphery. These elastically deformable elements have the effect, on the one hand, of absorbing the impacts and, on the other hand, of compensating for the necessary delay in the complete stopping of the machine in order to prevent, because of this time delay, the housing from reaching the element that has been collided with. As indicated above, it may be advisable, in the event of impact, to cause the mobile device 8 to reverse in order to clear away the element collided with.

Figure 3:
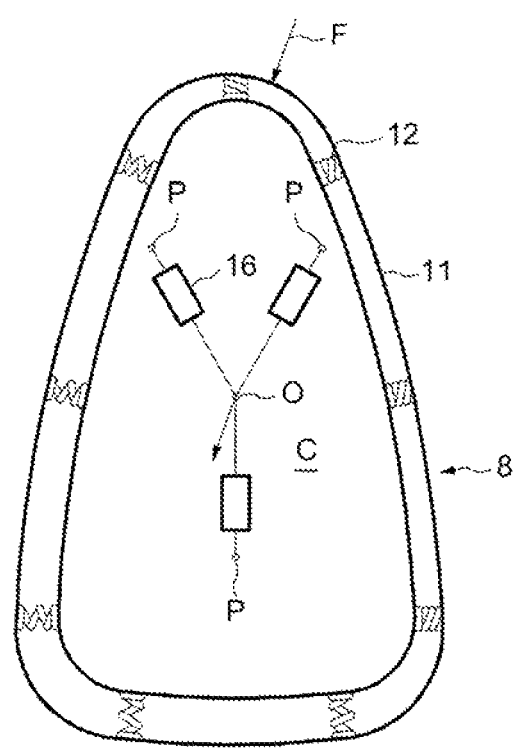
FIG. 3 shows the operating principle of the means of detection by triangulation according to an embodiment of the invention.

For this purpose, the anticollision system is also provided with detection means capable of detecting the direction of the force (arrow F) applied to the impact sensor 11 (FIG. 3). Various detection means can be used for this purpose. Triangulation, for example, may be used as the means of detection. It will be possible, for example, to use a set of linear potentiometers, such as 16, in this instance three in number, mounted on the one hand on a fixed point, such as P, linked to the housing C of the mobile device 8 and, on the other hand, to a common point 0 linked to a support of the impact sensor 11. In the event of impact, a measurement circuit detects the resulting change in resistance of each of the linear potentiometers 16, and converts this measurement into a corresponding distance measurement between each of the fixed points P and the central point 0 which is coupled to the impact sensor 11. These distance measurements make it possible to obtain, by direct triangulation, the change in position of the central point 0 and therefore the direction of application of the force. In this way the directional wheels and the driving means of the drive wheels of the mobile device 8 are directly controlled in order to cause a reverse movement and thus release the element collided with.

As can be understood, the embodiments of the present invention make it possible to detect impacts that might occur when the mobile device 8 moves. When the impact-sensing system is provided with detection means capable of detecting the direction of the applied force, it is also possible to achieve a reverse movement.

It will be noted that, in the embodiment in which a system of triangulation based on the use of potentiometers is used, the peripheral-impact sensor may be omitted because the means for detecting the direction of the impact also make it possible to detect the application of a force.

It will be noted finally that the invention is not limited to the embodiment described. The means of detection by triangulation, based on the use of linear potentiometers, may be replaced by any other type of triangulation device, for example based on the use of pulse encoders.

What is claimed is:

1. An X-ray machine, comprising:
an X-ray tube;
an X-ray detector placed opposite the X-ray tube in a direction of emission of X-rays; and
a mobile device on which the X-ray tube and the X-ray detector are mounted, the mobile device comprising a motor capable of causing movement of the mobile device, and an impact-sensing system configured to control the movement of the mobile device in the event of an impact applied to the mobile device, the impact-sensing system comprising a peripheral sensor mounted on a housing of the mobile device and extending along the entire periphery of the housing.

2. The X-ray machine according to claim 1, wherein the peripheral sensor comprises a resistive sensor.

3. The X-ray machine according to claim 1, wherein the impact-sensing system is mounted on a housing of the mobile device by a set of elastically deformable elements.

4. The X-ray machine according to claim 3, wherein the impact-sensing system is mounted on the housing by springs.

5. The X-ray machine according to claim 1, further comprising a detector configured to detect the force of impact applied to the X-ray machine.

6. The X-ray machine according to claim 5, wherein the detector is configured to detect the force of impact by triangulation.

7. The X-ray machine according to claim 6, wherein the detector configured to detect the force of impact by triangulation comprises:
- a set of elements configured to measure the movement of the impact-sensing system relative to three fixed points linked to the mobile device; and
- a measurement circuit configured to determine the direction of the force of impact as a function of the movement of the impact-sensing system.

8. The X-ray machine according to claim 7, wherein the set of elements comprises a set of linear potentiometers.

\* \* \* \* \*

UNITED STATES PATENT AND TRADEMARK OFFICE
CERTIFICATE OF CORRECTION

| | | |
|---|---|---|
| PATENT NO. | : 8,944,681 B2 | Page 1 of 1 |
| APPLICATION NO. | : 13/463057 | |
| DATED | : January 27, 2015 | |
| INVENTOR(S) | : Soto et al. | |

It is certified that error appears in the above-identified patent and that said Letters Patent is hereby corrected as shown below:

In the Specification

In Column 4, Line 27, delete "common point 0" and insert -- common point O --, therefor.

In Column 4, Line 32, delete "central point 0" and insert -- central point O --, therefor.

In Column 4, Line 35, delete "point 0" and insert -- point O --, therefor.

Signed and Sealed this
Tenth Day of November, 2015

Michelle K. Lee
*Director of the United States Patent and Trademark Office*